United States Patent
Sukegawa et al.

(10) Patent No.: US 9,594,253 B2
(45) Date of Patent: Mar. 14, 2017

(54) SPECTRAL APPARATUS, DETECTION APPARATUS, LIGHT SOURCE APPARATUS, REACTION APPARATUS, AND MEASUREMENT APPARATUS

(71) Applicants: CANON KABUSHIKI KAISHA, Tokyo (JP); The University of Tokyo, Tokyo (JP)

(72) Inventors: Takashi Sukegawa, Utsunomiya (JP); Yohei Kobayashi, Tokyo (JP); Akira Ozawa, Munich (DE); Mamoru Endo, Tokyo (JP); Makoto Gonokami, Tokyo (JP)

(73) Assignees: CANON KABUSHIKI KAISHA, Tokyo (JP); The University of Tokyo, Tokyo (JP)

( * ) Notice: Subject to any disclaimer, the term of this patent is extended or adjusted under 35 U.S.C. 154(b) by 129 days.

(21) Appl. No.: 14/294,480

(22) Filed: Jun. 3, 2014

(65) Prior Publication Data

US 2014/0363338 A1   Dec. 11, 2014

(30) Foreign Application Priority Data

Jun. 7, 2013   (JP) .................................. 2013-120520

(51) Int. Cl.
*G01N 21/00* (2006.01)
*G02B 27/10* (2006.01)
(Continued)

(52) U.S. Cl.
CPC ........ *G02B 27/1086* (2013.01); *G01J 1/0411* (2013.01); *G01J 1/0414* (2013.01);
(Continued)

(58) Field of Classification Search
CPC .................. G02B 27/1086; G02B 5/18; G02B 2005/1804; G01J 3/22; G01J 1/0414;
(Continued)

(56) References Cited

U.S. PATENT DOCUMENTS 6,278,534 B1   8/2001   Arns
6,524,237 B1 * 2/2003   McGowan .............. G02B 6/04
                                                            348/E7.087
(Continued)

FOREIGN PATENT DOCUMENTS

CN   103017904 A   4/2013
EP   1 308 704 A2   5/2003
(Continued)

OTHER PUBLICATIONS

Office Action issued in corresponding European Patent Application No. 14165535.7, dated Jan. 1, 2015.

*Primary Examiner* — Dennis M White
(74) *Attorney, Agent, or Firm* — Rossi, Kimms & McDowell LLP

(57) ABSTRACT

The present invention provides a spectral apparatus for spectrally separating light including a predetermined wavelength, including a slit that the light enters, a first optical system configured to collimate the light from the slit, a transmissive type diffraction element configured to diffract the light from the first optical system, and a second optical system including a first mirror configured to reflect the light diffracted by the transmissive type diffraction element, and a second mirror configured to reflect the light reflected by the first mirror and diffracted by the transmissive type diffraction element, and configured to make the light reciprocally travel between the first mirror and the second mirror via the transmissive type diffraction element.

14 Claims, 5 Drawing Sheets

(51) Int. Cl.
*G01J 3/28* (2006.01)
*G01J 3/18* (2006.01)
*G01N 21/75* (2006.01)
*G02B 5/18* (2006.01)
*G01J 3/02* (2006.01)
*G01J 1/04* (2006.01)
*G01J 3/22* (2006.01)

(52) U.S. Cl.
CPC ............. *G01J 1/0425* (2013.01); *G01J 3/021* (2013.01); *G01J 3/0208* (2013.01); *G01J 3/0221* (2013.01); *G01J 3/0291* (2013.01); *G01J 3/18* (2013.01); *G01J 3/1804* (2013.01); *G01J 3/22* (2013.01); *G01J 3/2823* (2013.01); *G01N 21/75* (2013.01); *G02B 5/18* (2013.01); *G01J 3/0218* (2013.01); *G01J 2003/1861* (2013.01); *G02B 2005/1804* (2013.01)

(58) Field of Classification Search
CPC ........ G01J 1/0411; G01J 3/021; G01J 3/0208; G01J 1/0425; G01J 3/0221; G01J 3/1804; G01J 3/0291; G01J 3/2823; G01J 3/18; G01J 2003/01; G01J 3/0218; G01J 2003/1861; G01N 21/75
See application file for complete search history.

(56) References Cited

U.S. PATENT DOCUMENTS

| | | | |
|---|---|---|---|
| 7,436,512 | B2 | 10/2008 | Ida et al. |
| 2001/0024275 | A1 | 9/2001 | Suzuki et al. |
| 2003/0081208 | A1 | 5/2003 | Kaneko et al. |
| 2005/0270376 | A1* | 12/2005 | Lin .......................... H04N 7/22 348/207.1 |
| 2006/0203859 | A1* | 9/2006 | Cable ...................... H01S 5/141 372/20 |
| 2012/0105837 | A1* | 5/2012 | Ingber ................ G01N 21/0303 356/246 |
| 2013/0163624 | A1 | 6/2013 | Miyanaga et al. |

FOREIGN PATENT DOCUMENTS

| | | |
|---|---|---|
| JP | 59-165017 A | 9/1984 |
| JP | 01-292221 A | 11/1989 |
| JP | 2006-162509 A | 6/2006 |
| JP | 2009-121986 A | 6/2009 |
| JP | 2010203860 A | 9/2010 |
| JP | 2011-257140 A | 12/2011 |
| WO | 2012/033105 A1 | 3/2012 |

\* cited by examiner

SPECTRAL APPARATUS, DETECTION APPARATUS, LIGHT SOURCE APPARATUS, REACTION APPARATUS, AND MEASUREMENT APPARATUS

BACKGROUND OF THE INVENTION

Field of the Invention

The present invention relates to a spectral apparatus, a detection apparatus, a light source apparatus, a reaction apparatus, and a measurement apparatus.

Description of the Related Art

The performance of a spectral apparatus is represented by the magnitude of a wavelength resolution ($\lambda/\Delta\lambda$). In particular, a high-resolution spectral apparatus is required to have a resolution more than 100,000. The theoretical critical resolution of a spectral apparatus using a diffraction element (diffraction grating) is uniquely determined depending on how much optical path difference can be ensured between the light components of respective wavelengths. Hence, to implement a high resolution in a spectral apparatus, a large diffraction element is necessary. For example, along with the progress of a high-repetition rate femtosecond laser or a high-output titanium sapphire femtosecond laser, a highly efficient transmissive type diffraction element as large as 150 mm or more is available nowadays. However, the actual resolution of the spectral apparatus is also limited by the incident size, imaging magnification, and optical aberrations of the spectral apparatus, and the resolution of a detector. In addition, when the diffraction element is made large, aberrations readily occur. It is therefore difficult to implement a high resolution by simply upsizing the diffraction element. Technologies associated with such a spectral apparatus have been proposed in Japanese Patent Laid-Open Nos. 2009-121986, 2006-162509, 1-292221, 2011-257140, and 59-165017.

On the other hand, an optical comb light source that outputs a train of optical pulses at temporally equal intervals has received attention in recent years. These pulses have a high phase relationship and interfere with each other. For this reason, the spectrum has a comb-shaped structure in which light components exactly apart by a predetermined frequency are arrayed at equal intervals. Such a comb-shaped spectral structure is generally called a longitudinal mode. Since the wavelengths of the longitudinal modes are slightly different, a spectral apparatus is used to spatially separate the longitudinal modes.

However, to actually separate the longitudinal modes, a spectral apparatus having a very high resolution is necessary. In addition, it is very difficult to implement a spectral apparatus capable of making a separated longitudinal mode usable as a light source. For example, the longitudinal mode interval of a generally available optical comb light source corresponds to an optical frequency of about 1 GHz. To separate the longitudinal modes of the optical comb light source, a spectral apparatus having a resolution more than at least 300,000 is necessary because the optical frequency is 300 THz. To implement such a resolution, the spectral apparatus needs to be constructed using a reflective type diffraction element larger than 300 mm, resulting in a bulky spectral apparatus.

If the longitudinal modes can be separated (extracted), a continuous wave light source or a light source capable of generating light of an arbitrary waveform can be implemented. Hence, the absolute efficiency (the ratio of input (amount of incident light) to the spectral apparatus to output (amount of light spectrally separated at a predetermined resolution)) of the spectral apparatus is very important. For the conventional spectral apparatus, however, improving the signal-to-noise ratio has priority in general from the viewpoint of detection accuracy. The absolute value of the output is rarely considered important, and techniques (arrangement and the like) for improving the absolute efficiently of the spectral apparatus are lesser known.

SUMMARY OF THE INVENTION

The present invention has, as its exemplary object, to provide a technique advantageously implementing downsizing, high resolution, and high efficiency of a spectral apparatus.

According to one aspect of the present invention, there is provided a spectral apparatus for spectrally separating light including a predetermined wavelength, including a slit that the light enters, a first optical system configured to collimate the light from the slit, a transmissive type diffraction element configured to diffract the light from the first optical system, and a second optical system including a first mirror configured to reflect the light diffracted by the transmissive type diffraction element, and a second mirror configured to reflect the light reflected by the first mirror and diffracted by the transmissive type diffraction element, and configured to make the light reciprocally travel between the first mirror and the second mirror via the transmissive type diffraction element, wherein the first optical system and the transmissive type diffraction element are arranged such that an incident angle of the light that enters the transmissive type diffraction element equals an exit angle of the light that exits from the transmissive type diffraction element, the first mirror is arranged such that an optical path of the light diffracted by the transmissive type diffraction element and traveling toward the first mirror and the optical path of the light reflected by the first mirror and traveling toward the transmissive type diffraction element exist in one first plane without overlapping each other in the first plane, and the second mirror is arranged such that the optical path of the light diffracted by the transmissive type diffraction element and traveling toward the second mirror and the optical path of the light reflected by the second mirror and traveling toward the transmissive type diffraction element exist in one second plane without overlapping each other in the second plane.

Further aspects of the present invention will become apparent from the following description of exemplary embodiments with reference to the attached drawings.

DESCRIPTION OF THE EMBODIMENTS

Figure 1:
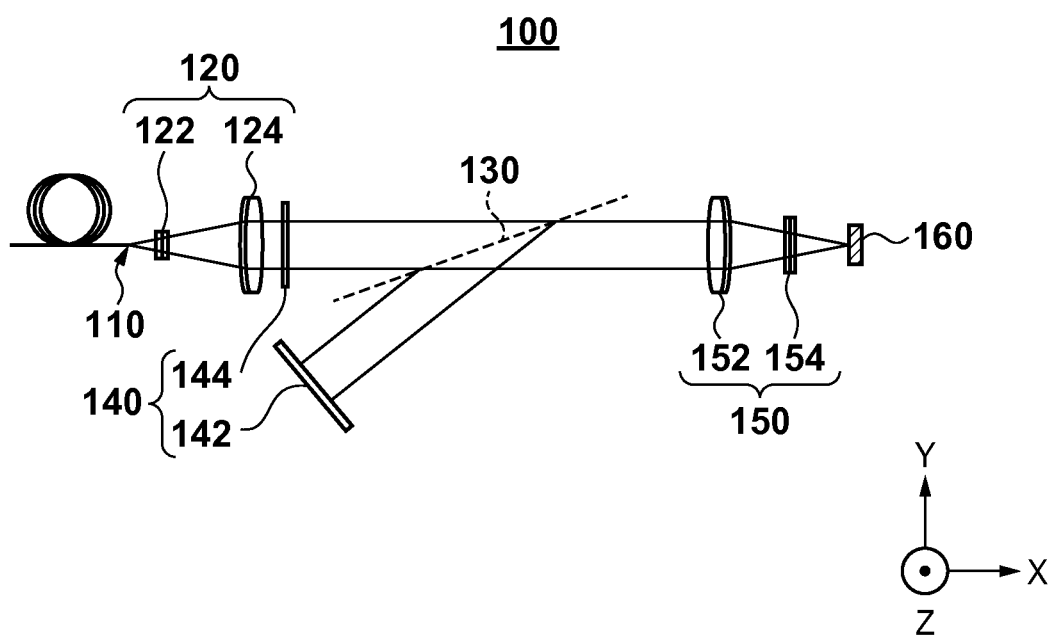
FIG. 1 is a schematic view showing the arrangement of a detection apparatus according to an aspect of the present invention.

Preferred embodiments of the present invention will be described below with reference to the accompanying drawings. Note that the same reference numerals denote the same members throughout the drawings, and a repetitive description thereof will not be given.

First Embodiment

FIG. 1 is a schematic view showing the arrangement of a detection apparatus 100 according to an aspect of the present invention. The detection apparatus 100 includes a slit 110, a first optical system 120, a transmissive type diffraction element 130, a second optical system 140, an imaging optical system 150, and a detector 160. In the detection apparatus 100, the slit 110, the first optical system 120, the transmissive type diffraction element 130, and the second optical system 140 constitute a spectral apparatus for spectrally separating light that includes a predetermined wavelength and is emitted by a light source as a detection target, as will be described later.

Referring to FIG. 1, light emitted by the light source is guided to the detection apparatus 100 via a single-mode fiber having a mode field diameter of, for example, 6 µm. In this embodiment, the exit port of the single-mode fiber functions as a slit, that is, the slit 110 (a member having a slit-like opening or light transmitting portion) that the light from the light source enters. The light from the single-mode fiber (the light from the slit 110) enters the first optical system 120.

The first optical system 120 is a collimating optical system including a cylindrical lens 122 and an achromatic cylindrical lens 124 and configured to collimate the light from the slit 110. The cylindrical lens 122 has an enlargement ratio asymmetrical (that is, different in two directions perpendicular to each other) in a section perpendicular to the light traveling direction. The first optical system 120 enlarges the light from the slit 110 by the first magnification in the repeating direction of the grating of the transmissive type diffraction element 130 and by the second magnification lower than the first magnification in a direction perpendicular to the repeating direction of the grating of the transmissive type diffraction element 130, and at the same time collimates the light. The achromatic cylindrical lens 124 is formed by, for example, combining two types of lenses, a lens made of a low dispersion material and a lens made of a high dispersion material, and has a function of reducing imaging aberrations.

In this embodiment, the light from the slit 110 is collimated into light of 1 mm in the vertical direction (the direction perpendicular to the repeating direction of the grating of the transmissive type diffraction element 130)×25 mm in the horizontal direction (the repeating direction of the grating of the transmissive type diffraction element 130) via the first optical system 120. The first optical system 120 makes the collimated light obliquely enter the transmissive type diffraction element 130.

The transmissive type diffraction element 130 is a diffraction grating that diffracts the light from the first optical system 120. The transmissive type diffraction element 130 is formed from, for example, a diffraction grating having a diffraction efficiency of 90% or more and a size of 180 mm in the repeating direction of the grating. In this embodiment, the light from the first optical system 120 enters the transmissive type diffraction element 130 at an angle (incident angle) α obtained from an equation represented by mλ=2d·sin α, where λ is a predetermined wavelength, d is the grating pitch of the transmissive type diffraction element 130, and m is an integer (order) of 1 or more. The above-described equation means that the first optical system 120 and the transmissive type diffraction element 130 are arranged such that the incident angle of the light that enters the transmissive type diffraction element 130 equals the exit angle of the light that exits from the transmissive type diffraction element 130. In other words, the transmissive type diffraction element 130 has a Littrow arrangement.

The second optical system 140 includes a first mirror 142 that reflects light diffracted by the transmissive type diffraction element 130, and a second mirror 144 that reflects light reflected by the first mirror 142 and further diffracted by the transmissive type diffraction element 130. The second optical system 140 is an optical system configured to make light reciprocally travel between the first mirror 142 and the second mirror 144 via the transmissive type diffraction element 130 (that is, cause the transmissive type diffraction element 130 to diffract the light from the first optical system 120 many times).

Each of the first mirror 142 and the second mirror 144 is formed from a plane mirror having a high reflectance to light from the light source as the detection target. The optical path of light diffracted by the transmissive type diffraction element 130 and traveling toward the first mirror 142 will be defined as a first optical path, and the optical path of light reflected by the first mirror 142 and traveling toward the transmissive type diffraction element 130 as a second optical path. In this case, the first mirror 142 is arranged such that the first optical path and the second optical path exist in one first plane without overlapping each other in the first plane. The optical path of light diffracted by the transmissive type diffraction element 130 and traveling toward the second mirror 144 will be defined as a third optical path, and the optical path of light reflected by the second mirror 144 and traveling toward the transmissive type diffraction element 130 as a fourth optical path. In this case, the second mirror 144 is arranged such that the third optical path and the fourth optical path exist in one second plane without overlapping each other in the second plane.

The imaging optical system 150 includes an achromatic cylindrical lens 152 and a cylindrical lens 154, and forms an image of 0th-order light (transmission diffracted light) transmitted through the transmissive type diffraction element 130 without being diffracted on (the detection surface of) the detector 160. The achromatic cylindrical lens 152 and the cylindrical lens 154 have the same arrangements as those of, for example, the achromatic cylindrical lens 124 and the cylindrical lens 122, respectively, and any arrangements known in the industry are applicable.

The detector 160 is formed from, for example, a CCD sensor having a plurality of pixels that are two-dimensionally arrayed, and detects the intensity of the 0th-order light transmitted through the transmissive type diffraction element 130, that is, the 0th-order light whose image is formed by the imaging optical system 150.

In the detection apparatus 100, and the second optical system 140 (first mirror 142 and second mirror 144) causes the transmissive type diffraction element 130 to diffract the light collimated by the first optical system 120 many times. Every time the transmissive type diffraction element 130 diffracts the light, 0th-order light transmitted through the transmissive type diffraction element 130 is extracted. The 0th-order light is focused (spectrally separated) on the detector 160 via the imaging optical system 150. The detector 160 detects the intensity of the light.

Figure 2:
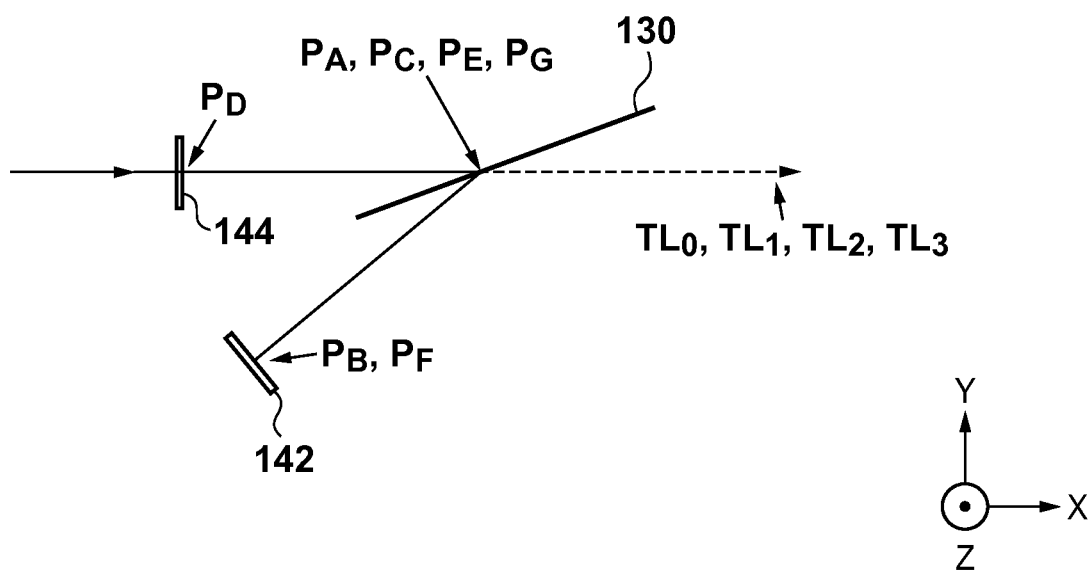
FIG. 2 is a view for explaining the optical path of light that reciprocally travels between the first mirror and the second mirror of the detection apparatus shown in FIG. 1.
Figure 3:
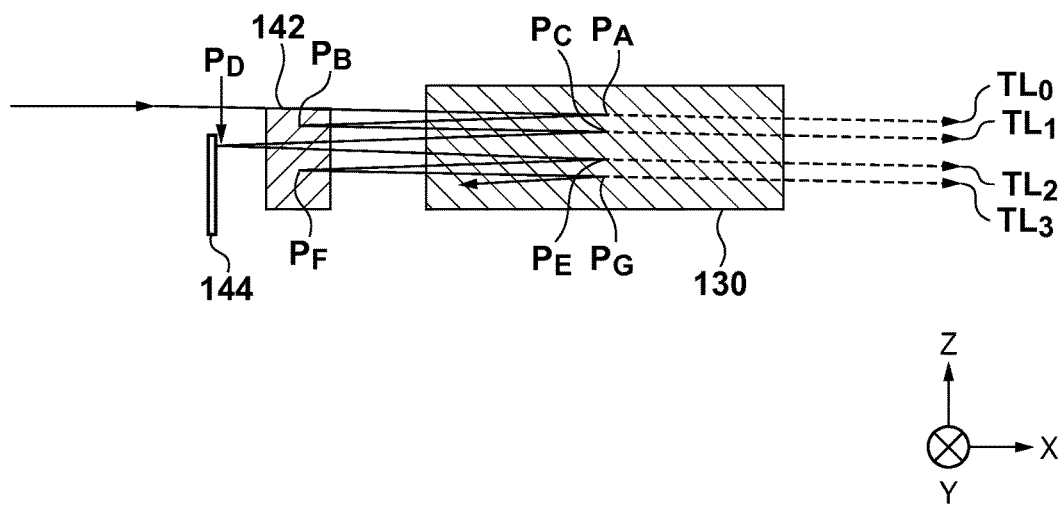
FIG. 3 is a view for explaining the optical path of light that reciprocally travels between the first mirror and the second mirror of the detection apparatus shown in FIG. 1.

The optical path of light that reciprocally travel between the first mirror 142 and the second mirror 144 will be described with reference to FIGS. 2 and 3. FIGS. 2 and 3 are respectively an X-Y plane view and an X-Z plane view showing a portion around the transmissive type diffraction element 130, the first mirror 142, and the second mirror 144.

Referring to FIGS. 2 and 3, the light collimated by the first optical system 120 passes above the second mirror 144 and enters the transmissive type diffraction element 130. At this time, since the transmissive type diffraction element 130 is arranged vertically, the light from the first optical system 120 enters the transmissive type diffraction element 130 obliquely, that is, in a state having an angle (directed downward) in the Z direction, as described above. The light that has entered the transmissive type diffraction element 130 is diffracted at a point $P_A$ on it. Then, 1st-order diffracted light enters the first mirror 142 and is reflected at a point $P_B$ on it. At this time, since the 1st-order diffracted light enters the first mirror 142 in a downward-directed state, the light reflected at the point $P_B$ on the first mirror also enters the transmissive type diffraction element 130 in a downward-directed state. Hence, the light reflected at the point $P_B$ on the first mirror enters a point $P_C$ different (displaced in the Z direction) from the point $P_A$ on the transmissive type diffraction element. The light that has entered the transmissive type diffraction element 130 is diffracted at the point $P_C$ on it. Then, 1st-order diffracted light enters the second mirror 144 and is reflected at a point $P_D$ on it. At this time, since the 1st-order diffracted light enters the second mirror 144 in a downward-directed state, the light reflected at the point $P_D$ on the second mirror also enters the transmissive type diffraction element 130 in a downward-directed state. Hence, the light reflected at the point $P_D$ on the second mirror enters a point $P_E$ different (displaced in the Z direction) from the point $P_C$ on the transmissive type diffraction element. By repeating this, the light from the first optical system 120 travels while being displaced in the Z direction in the order of the points $P_A$, $P_B$, $P_C$, $P_D$, $P_E$, $P_F$, $P_G$, . . . .

On the other hand, 0th-order light transmitted through the transmissive type diffraction element 130 without being diffracted appears as 0th-order light components $TL_0$, $TL_1$, $TL_2$, $TL_3$, . . . in accordance with the diffraction count on the transmissive type diffraction element 130 and is detected by the detector 160 via the imaging optical system 150. Note that each subscript of the 0th-order light components $TL_0$, $TL_1$, $TL_2$, $TL_3$, . . . indicates the "number of times of diffraction by the transmissive type diffraction element 130". Hence, every time light is diffracted by the transmissive type diffraction element 130, the 0th-order light components $TL_0$, $TL_1$, $TL_2$, $TL_3$, . . . transmitted through the transmissive type diffraction element 130 are separated in the Z direction, as is apparent. The 0th-order light components $TL_0$, $TL_1$, $TL_2$, $TL_3$, . . . transmitted through the transmissive type diffraction element 130 are parallel to each other. The intervals are determined by the positional relationship between the transmissive type diffraction element 130, the first mirror 142, and the second mirror 144, and are not necessarily equal. To obtain the 0th-order light components $TL_0$, $TL_1$, $TL_2$, $TL_3$, . . . at equal intervals, the distance between the transmissive type diffraction element 130 and the first mirror 142 is made equal to that between the transmissive type diffraction element 130 and the second mirror 144.

As described above, in this embodiment, the transmissive type diffraction element 130 is used in the Littrow arrangement. The necessity and advantage of making the transmissive type diffraction element 130 have the Littrow arrangement will be described below.

The diffraction efficiency of the transmissive type diffraction element 130 is maximum in the Littrow arrangement. Hence, to maximize the efficiency of a spectral apparatus using the transmissive type diffraction element 130, the transmissive type diffraction element 130 needs to have the Littrow arrangement. In this embodiment, since the light from the first optical system 120 passes through the transmissive type diffraction element 130 many times, it is important to make the transmissive type diffraction element 130 have the Littrow arrangement.

The transmissive type diffraction element 130 is distorted in actuality due to the influence of a change in temperature or the like. The distortion of the transmissive type diffraction element 130 cannot be neglected when implementing a spectral apparatus having a high resolution of 300,000 or more. However, when the transmissive type diffraction element 130 has the Littrow arrangement, the sensitivity to the distortion of the transmissive type diffraction element 130 is minimized. It is therefore possible to use the transmissive type diffraction element 130 without any special consideration.

Figure 4A:
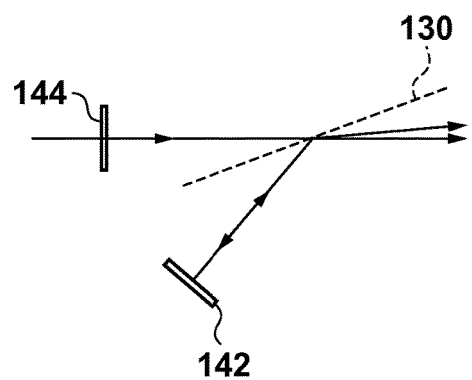
FIGS. 4A and 4B are views for explaining the necessity and advantage of making the transmissive type diffraction element of the detection apparatus shown in FIG. 1 have a Littrow arrangement.
Figure 4B:
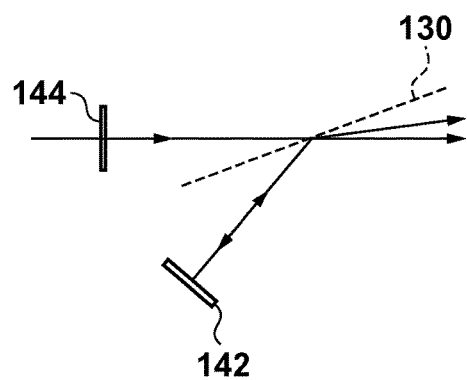

Since the incident angle of light that enters the transmissive type diffraction element 130 equals the exit angle of light that exits from the transmissive type diffraction element 130, the light transmitted through the transmissive type diffraction element 130 and the light reflected by the transmissive type diffraction element 130 exit in the same direction, as shown in FIG. 4A. This makes it possible to form the image of the light from the transmissive type diffraction element 130 by one imaging optical system 150. On the other hand, if the incident angle of light that enters the transmissive type diffraction element 130 and the exit angle of light that exits from the transmissive type diffraction element 130 are different, the light transmitted through the transmissive type diffraction element 130 and the light reflected by the transmissive type diffraction element 130 exit in different directions, as shown in FIG. 4B. It is therefore impossible to form the image of the light from the transmissive type diffraction element 130 by one imaging optical system 150, and two imaging optical systems (an imaging optical system that forms an image of light transmitted through the transmissive type diffraction element 130 and an imaging optical system that forms an image of light reflected by the transmissive type diffraction element 130) are needed.

Figure 5:
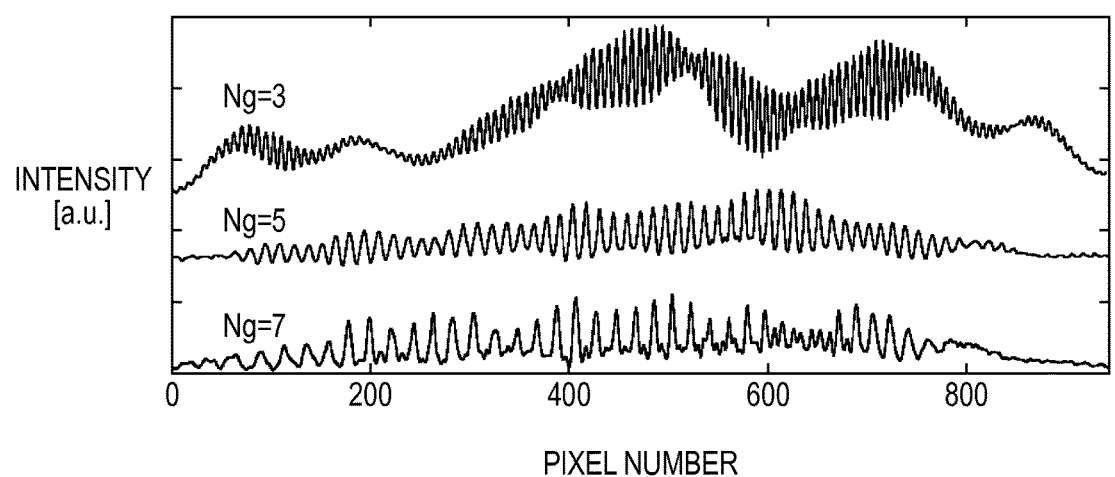
FIG. 5 is a graph showing an example of fringes detected by the detection apparatus shown in FIG. 1.
Figure 6:
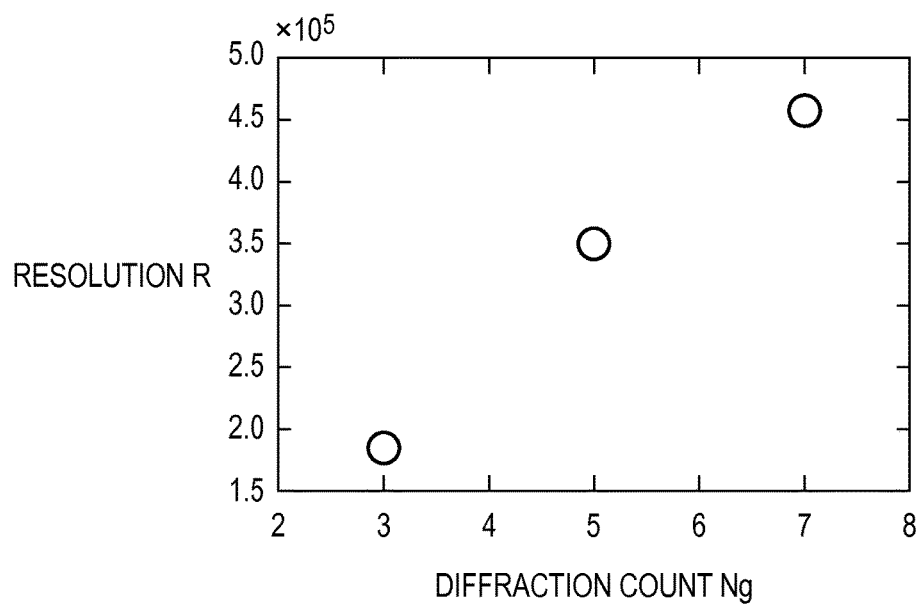
FIG. 6 is a graph showing the relationship between the diffraction count and the resolution of the transmissive type diffraction element of the detection apparatus shown in FIG. 1.

When light from a mode-locked laser having a repetitive frequency of 2.5 GHz enters the detection apparatus 100, fringes as shown in FIG. 5 are detected. In FIG. 5, the pixel number of the detector 160 is employed on the abscissa, and the intensity detected by the detector 160 is employed on the ordinate. Assume that the cylindrical lenses 122 and 154 have focal lengths of 15 mm and 50 mm, respectively, and the achromatic cylindrical lenses 124 and 152 have a focal length of 250 mm. Also assume that the size and pitch of the transmissive type diffraction element 130 are 180 mm×40 mm and 1,740 g/mm. As is apparent from FIG. 5, as a diffraction count Ng of the transmissive type diffraction element 130 increases, the fringe interval widens, that is, the spatial resolution improves. FIG. 6 shows the relationship between the diffraction count Ng and a resolution R of the transmissive type diffraction element 130. In FIG. 6, the diffraction count Ng of the transmissive type diffraction element 130 is employed on the abscissa, and the resolution R is employed on the ordinate. As is apparent from FIG. 6, when the diffraction count Ng of the transmissive type diffraction element 130 is 5, the resolution R exceeds 350,000.

As described above, according to this embodiment, when spectrally detecting light at a wavelength of 1 µm, a longitudinal mode of 1 GHz or less can be separated and detected by setting the diffraction count of the transmissive type diffraction element 130 to 5 or more. The diffraction efficiency is 30% or more, and the evaluation size is smaller than 1 m×0.5 m. Size reduction and a high efficiency can be attained as compared to a spectral apparatus using a reflective type diffraction element having equal performance.

When an optical comb light source having a longitudinal mode interval that can spatially be separated by the detector 160 is used as the light source as the detection target, the detection apparatus 100 can detect the intensity of light from the optical comb light source for each wavelength (that is, each longitudinal mode). In this case, since the wavelength of light of each longitudinal mode of the optical comb light source can accurately be detected, the spectral apparatus can be calibrated based on the wavelength. For example, when both target light and light from the optical comb light source enter the detection apparatus 100, the detector 160 spectrally detects both the target light and the light of the longitudinal mode of the optical comb light source. It is therefore possible to accurately obtain the wavelength of the target light by comparing the position of the target light on the detector with the position of the light of the longitudinal mode of the optical comb light source.

Second Embodiment

A light source apparatus can be formed by combining an optical comb light source and a spectral apparatus including a slit 110, a first optical system 120, a transmissive type diffraction element 130, and a second optical system 140.

Figure 7:
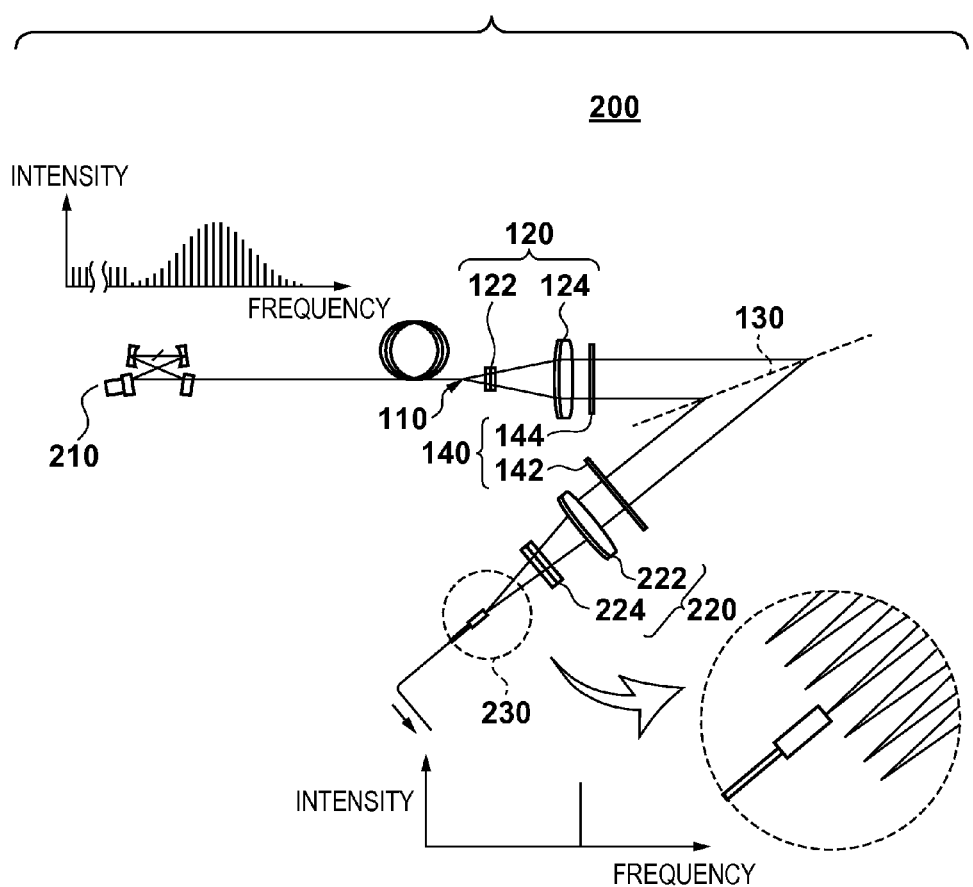
FIG. 7 is a schematic view showing the arrangement of a light source apparatus according to an aspect of the present invention.

FIG. 7 is a schematic view showing the arrangement of a light source apparatus 200 according to an aspect of the present invention. The light source apparatus 200 includes an optical comb light source 210, the slit 110, the first optical system 120, the transmissive type diffraction element 130, the second optical system 140, an imaging optical system 220, and an extraction unit 230. The light source apparatus 200 separates light components of respective longitudinal modes of the optical comb light source 210, extracts light of one longitudinal mode or light components of a plurality of longitudinal modes, and uses the light as a light source.

The optical comb light source 210 is formed from a high-repetition rate mode-locked laser of 1 GHz or more. In this embodiment, the optical comb light source 210 emits light having longitudinal mode intervals that can spatially be separated, for example, light having a spectrum as shown on the upper left of FIG. 7.

Light from the optical comb light source 210 enters the first optical system 120 via the exit port of a single-mode fiber, that is, the slit 110. The light that has entered the first optical system 120 is collimated and reciprocally travels between a first mirror 142 and a second mirror 144 via the transmissive type diffraction element 130, as described above.

The imaging optical system 220 includes an achromatic cylindrical lens 222 and a cylindrical lens 224, and forms an image of light of a longitudinal mode that has stopped entering the first mirror 142 by repetitively reciprocally traveling in the second optical system 140.

The extraction unit 230 is arranged on the imaging plane of the imaging optical system 220, and has a function of extracting light of the longitudinal mode whose image is formed by the imaging optical system 220. In this embodiment, the extraction unit 230 is formed from a single-mode fiber (optical fiber) arranged at a position where the imaging optical system 220 forms an image of light of a longitudinal mode corresponding to a predetermined wavelength out of the light components of the plurality of longitudinal modes included in the light from the optical comb light source 210. The extraction unit 230 may be formed from a plurality of single-mode fibers arranged at a plurality of positions where the imaging optical system 220 forms images of the light components of the plurality of longitudinal modes included in the light from the optical comb light source 210.

With the above-described arrangement, the light source apparatus 200 can separate the light of each longitudinal mode of the optical comb light source 210 and extract light of one or a plurality of longitudinal modes, as shown on the lower right of FIG. 7. Hence, the light source apparatus 200 forms a continuous wave (CW) light source of a specific frequency using the light of a longitudinal mode as a secondary light source. Note that it is also possible to form continuous wave light sources of various wavelengths by changing the light of one or a plurality of longitudinal modes to be extracted.

In the first embodiment, an example in which 0th-order light transmitted through the transmissive type diffraction element 130 is used has been described. However, to extract strongest light, the arrangement as shown in FIG. 7 is used. More specifically, the first mirror 142 is arranged not to interfere with light whose diffraction count has reached a value at which a predetermined dispersion can be obtained, and the imaging optical system is caused to form an image of light that has passed the first mirror 142 without being totally reflected (that is, light that has stopped entering the first mirror 142). When a single-mode fiber configured to extract light of a predetermined longitudinal mode is arranged at the imaging position of the imaging optical system, a light source including light of one specific longitudinal mode or light components of a plurality of specific longitudinal modes can be formed.

The light source apparatus 200 is applicable to a measurement apparatus such as an optical wavelength measurement apparatus for accurately measuring the wavelength of light absorbed by an object. An atom or molecule has a property of absorbing light of a specific wavelength. To correctly measure the absorption wavelength, it is necessary to irradiate an object with light having a wavelength accurately calibrated and detect a wavelength of maximum absorption while scanning the wavelength of the light. Hence, to measure the wavelength of light absorbed by the object, the light source apparatus 200 that extracts light of one longitudinal mode from the optical comb light source and uses it as a light source is suitable. This measurement apparatus includes an optical system that irradiates an object with light from the light source apparatus 200, a device (for example, ion trap or cooling device) that controls the temperature distribution or speed distribution of the object, and a container (for example, vacuum chamber or discharge gas cell) that maintains the object in an appropriate environment. The measurement apparatus also includes a measurement unit that measures information of a light component absorbed by the object out of the light that has irradiated the object. The measurement unit includes, for example, a device that measures the quantity of ions generated by absorption, a device that measures the intensity of light decreased by absorption, and a device that measures the intensity of fluorescence generated by absorption. The measurement apparatus also includes a device that changes the optical frequency of the optical comb light source (for example, a device that changes the cavity length or excitation light intensity of the optical comb light source).

The light source apparatus 200 is also applicable to an optical comb generation apparatus (light source) that stabilizes the wavelength of light to be emitted. The optical comb light source is a laser light source including light components of longitudinal modes arranged at equal intervals. The wavelengths of the light components of the longitudinal modes may include a slight temporal fluctuation. To suppress the fluctuation, light of one longitudinal mode is extracted from the optical comb light source, and the optical comb light source is controlled (adjusted) to make the wavelength of the light constant. To make the wavelength of the extracted light of one longitudinal mode constant, a resonator is used. The wavelength with which the resonator causes resonance is determined by the interval of two mirrors included in the resonator. Hence, the optical comb light source is controlled by the resonator including the two mirrors having a stable interval such that the extracted light of one longitudinal mode always meets the resonance condition of the resonator. This optical comb generation apparatus includes a resonator whose length does not change, an adjustment unit (for example, optical amplifier or optical attenuator) that adjusts light extracted by the light source apparatus 200 to an intensity suitable for the resonator, and a detection unit that detects whether the resonance condition of the resonator is met. The detection unit includes a device that measures the intensity of light transmitted by the resonator, a device that measures the intensity of light reflected by the resonator, a device that measures the special mode of light reflected by the resonator, and a device that measures the polarization of light reflected by the resonator. The optical comb generation apparatus further includes a control unit that performs feedback control of the optical frequency of the optical comb light source by, for example, changing the cavity length or excitation light intensity of the optical comb light source.

Third Embodiment

Figure 8:
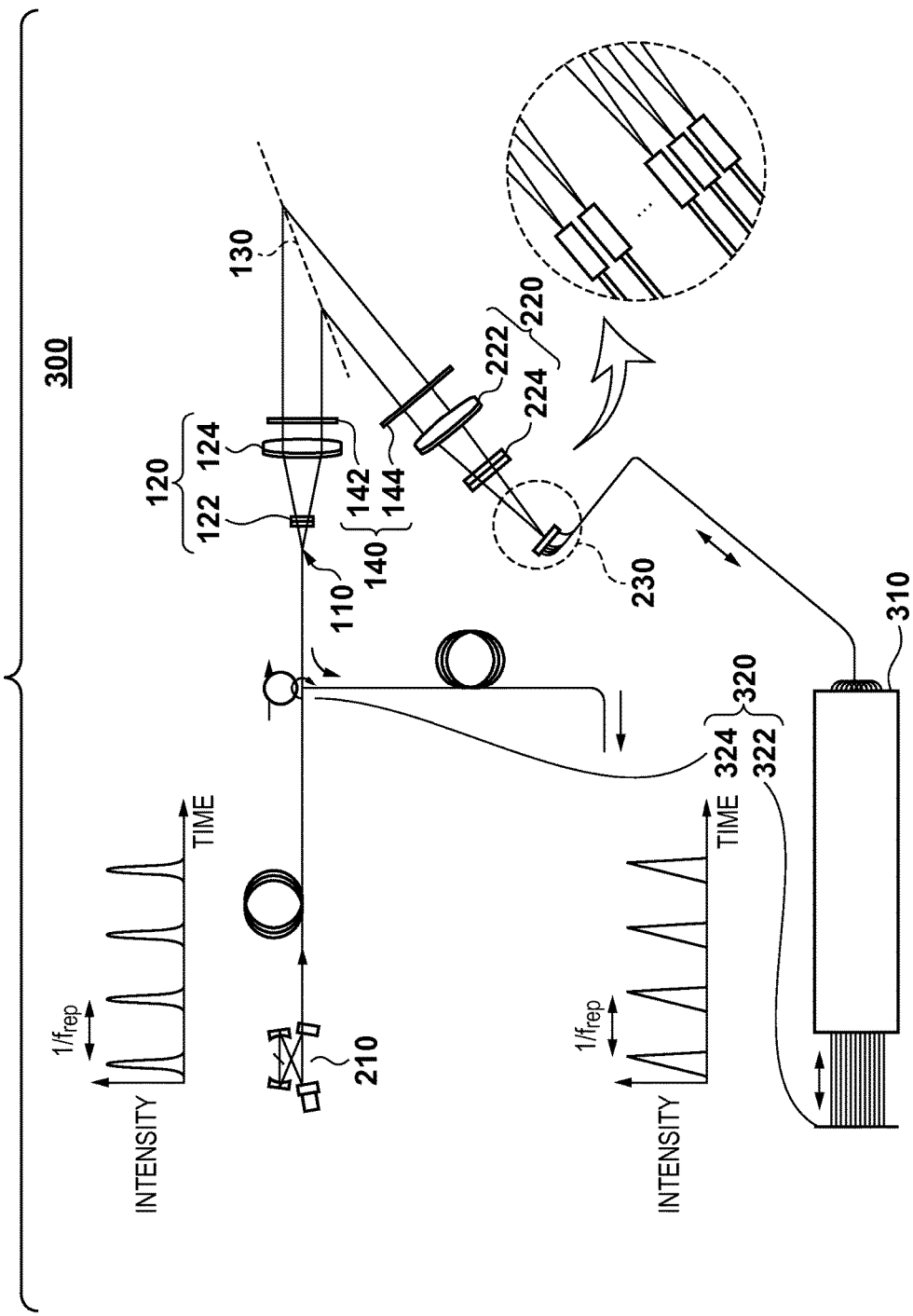
FIG. 8 is a schematic view showing the arrangement of a light source apparatus according to an aspect of the present invention.

FIG. 8 is a schematic view showing the arrangement of a light source apparatus 300 according to an aspect of the present invention. The light source apparatus 300 includes an optical comb light source 210, a slit 110, a first optical system 120, a transmissive type diffraction element 130, a second optical system 140, an imaging optical system 220, an extraction unit 230, a modulation unit 310, and a combining unit 320. The light source apparatus 300 separates light components of respective longitudinal modes of the optical comb light source 210, modulates and combines the light components of the longitudinal modes, thereby generating light of an arbitrary waveform.

The optical comb light source 210 is formed from a high-repetition rate mode-locked laser of 1 GHz or more. In this embodiment, the optical comb light source 210 emits light having longitudinal mode intervals that can spatially be separated, for example, in a shape as shown on the upper left of FIG. 7.

Light from the optical comb light source 210 enters the first optical system 120 via the exit port of a single-mode fiber, that is, the slit 110. The light that has entered the first optical system 120 is collimated and reciprocally travels between a first mirror 142 and a second mirror 144 via the transmissive type diffraction element 130, as described above.

The imaging optical system 220 includes an achromatic cylindrical lens 222 and a cylindrical lens 224, and forms an image of light of a longitudinal mode that has stopped entering the first mirror 142 by repetitively reciprocally traveling in the second optical system 140.

In this embodiment, the extraction unit 230 is formed from a plurality of single-mode fibers corresponding to light components of a plurality of longitudinal modes to extract each of the light components of the plurality of longitudinal modes included in the light from the optical comb light source 210.

The modulation unit 310 modulates each of the light components of the plurality of longitudinal modes extracted by the extraction unit 230. More specifically, the modulation unit 310 changes the intensity and phase of each of the light components of the plurality of longitudinal modes extracted by the extraction unit 230 such that the light combined by the combining unit 320 has a predetermined shape.

The combining unit 320 has a function of combining the light components of the plurality of longitudinal modes modulated by the modulation unit 310. In this embodiment, the combining unit 320 includes a third mirror 322 that reflects each of the light components of the plurality of longitudinal modes modulated by the modulation unit 310, and a circulator 324 that separates the combined light of the light components of the plurality of longitudinal modes reflected by the third mirror 322.

The third mirror 322 reflects each of the light components of the plurality of longitudinal modes modulated by the modulation unit 310 such that each of the light components of the plurality of longitudinal modes modulated by the modulation unit 310 returns to the optical path until it enters the third mirror 322. The circulator 324 is arranged between the optical comb light source 210 and the slit 110 and separates the combined light of the plurality of longitudinal modes reflected by the third mirror 322. Through this path, the light components of the plurality of longitudinal modes modulated by the modulation unit 310 go through a process reverse to the spatial separation process and are spatially combined again. Hence, the combining unit 320 need only give the optical path difference given in the spatial separation process. For example, instead of using the third mirror 322 and the circulator 324, the optical path from the extraction unit 230 to the slit 110 may be arranged at the subsequent stage of the modulation unit 310.

With this arrangement, the light source apparatus 300 can separate the light of each longitudinal mode of the optical comb light source 210 and modulate and combine the light components of the respective longitudinal modes, thereby generating light of an arbitrary waveform, as shown in middle left of FIG. 8. Hence, the light source apparatus 300 can emit light of various waveforms using the light of such an arbitrary waveform as a secondary light source.

In the first embodiment, an example in which 0th-order light transmitted through the transmissive type diffraction element 130 is used has been described. However, to extract strongest light, the arrangement as shown in FIG. 8 is used.

More specifically, the first mirror 142 is arranged not to interfere with light whose diffraction count has reached a value at which a predetermined dispersion can be obtained, and the imaging optical system is caused to form an image of light that has passed the first mirror 142 without being totally reflected (that is, light that has stopped entering the first mirror 142). When a plurality of single-mode fibers configured to extract light components of the respective longitudinal modes are arranged at the imaging position of the imaging optical system, and the light components of the longitudinal modes are combined after adjusting the intensity and phase of each light component, light of an arbitrary waveform can be generated.

The light source apparatus 300 is applicable to, for example, a reaction apparatus such as photoinduced reaction control apparatus. When atoms or molecules are irradiated with light (optical field), various kinds of reactions (photoinduced reactions) can be caused by the light. Such a reaction depends on the waveform of light and can be controlled by appropriately controlling (shaping) the waveform (coherence control). More specifically, a product can efficiently be generated by freely changing absorption or molecular vibration excitation efficiency or controlling the chemical reaction of light induction. This reaction apparatus includes an optical system that efficiently irradiates an object with light from the light source apparatus 300, a container that an environment suitable for a reaction caused by light irradiation, and a measurement unit that measures at least one of the reaction rate and reaction state of the object. The above-described container includes, for example, a cooling chamber, a heating chamber, and a vacuum chamber. The above-described measurement unit includes, for example, a device that measures the amount of a reaction product, and a device that measures a change in the intensity of light (optical field) by a reaction. The reaction apparatus may further include a control unit that performs feedback control of the modulation amount (intensity or phase adjustment amount) of light of each longitudinal mode so that a target reaction takes place based on the measurement result of the measurement unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-120520 filed on Jun. 7, 2013, which is hereby incorporated by reference herein in its entirety.

What is claimed is:

1. An apparatus comprising:
   a slit that light enters;
   a first optical system configured to collimate the light from the slit;
   a transmissive type diffraction element configured to diffract the light from the first optical system; and
   a second optical system including a first mirror configured to reflect the light diffracted by the transmissive type diffraction element, and a second mirror configured to reflect the light reflected by the first mirror and diffracted by the transmissive type diffraction element, and configured to make the light reciprocally travel between the first mirror and the second mirror via the transmissive type diffraction element,
   wherein the first optical system and the transmissive type diffraction element are arranged such that an incident angle of the light that enters the transmissive type diffraction element equals an exit angle of the light that exits from the transmissive type diffraction element,
   the first mirror is arranged such that an optical path of the light diffracted by the transmissive type diffraction element and traveling toward the first mirror and an optical path of the light reflected by the first mirror and traveling toward the transmissive type diffraction element exist in one first plane without overlapping each other in the first plane, and
   the second mirror is arranged such that an optical path of the light diffracted by the transmissive type diffraction element and traveling toward the second mirror and an optical path of the light reflected by the second mirror and traveling toward the transmissive type diffraction element exist in one second plane without overlapping each other in the second plane.

2. The apparatus according to claim 1, wherein the first optical system enlarges the light from the slit by a first magnification in a repeating direction of a grating of the transmissive type diffraction element and by a second magnification lower than the first magnification in a direction perpendicular to the repeating direction.

3. The apparatus according to claim 1, additionally comprising:
   a detector including a plurality of pixels configured to detect an intensity of diffracted light transmitted through the transmissive type diffraction element; and
   an imaging optical system configured to form an image of the transmission diffracted light on the plurality of pixels.

4. The apparatus according to claim 3, wherein the plurality of pixels are two-dimensionally arrayed.

5. The apparatus according to claim 3, wherein the light including the predetermined wavelength comprises light from an optical comb light source having a longitudinal mode interval that can spatially be separated by the detector, and
   the detector detects the intensity for each wavelength of the light from the optical comb light source.

6. The apparatus according to claim 1, additionally comprising:
   an optical comb light source configured to emit light including the predetermined wavelength and having a longitudinal mode interval that can spatially be separated;
   an imaging optical system configured to form an image of light of a longitudinal mode that stops entering said first mirror by repetitively reciprocally traveling in the second optical system; and
   an extraction unit arranged on an imaging plane of the imaging optical system and configured to extract the light of the longitudinal mode whose image has been formed by the imaging optical system.

7. The apparatus according to claim 6, wherein the extraction unit includes an optical fiber arranged at a position where the imaging optical system forms an image of light of a longitudinal mode corresponding to the predetermined wavelength out of light components of a plurality of longitudinal modes included in the light from the optical comb light source.

8. The apparatus according to claim 6, wherein the extraction unit includes a plurality of optical fibers arranged at a plurality of positions where the imaging optical system forms images of light components of a plurality of longitudinal modes included in the light from the optical comb light source.

9. The apparatus according to claim 6, wherein the extraction unit extracts each of light components of a plurality of longitudinal modes included in the light from the optical comb light source,
the apparatus further comprising:
a modulation unit configured to modulate each of the light components of the plurality of longitudinal modes extracted by the extraction unit; and
a combining unit configured to combine the light components of the plurality of longitudinal modes modulated by the modulation unit.

10. The apparatus according to claim 9, wherein the modulation unit modulates each of the light components of the plurality of longitudinal modes extracted by the extraction unit such that the light combined by the combining unit has a predetermined shape.

11. The apparatus according to claim 9, wherein the combining unit includes:
a third mirror configured to reflect each of the light components of the plurality of longitudinal modes modulated by the modulation unit; and
a circulator configured to separate combined light of the plurality of longitudinal modes reflected by the third mirror,
the third mirror reflects each of the light components of the plurality of longitudinal modes modulated by the modulation unit such that each of the light components of the plurality of longitudinal modes modulated by the modulation unit returns to an optical path until the light component enters the third mirror, and
the circulator is arranged between the optical comb light source and the slit.

12. The apparatus according to claim 9, additionally comprising:
an optical system configured to irradiate an object with light emitted by the light source apparatus; and
a measurement unit configured to measure at least one of a reaction rate and a reaction state of the object by light irradiation from the optical system.

13. The apparatus according to claim 7, additionally comprising:
an optical system configured to irradiate an object with light emitted by the light source apparatus; and
a measurement unit configured to measure information about light absorbed by the object out of the light with which the optical system irradiates the object.

14. The apparatus according to claim 6, further comprising:
an adjustment unit configured to adjust an intensity of the light emitted by the optical comb light source such that at least one of a plurality of longitudinal modes obtained by the light source apparatus has a predetermined wavelength.

* * * * *